United States Patent [19]

Hajos et al.

[11] 4,310,549

[45] Jan. 12, 1982

[54] TREATMENT OF HYPERTENSION WITH 1-TERT.-BUTYLAMINO-3-(2,5-DICHLOROPHENOXY)-2-PROPANOL

[76] Inventors: Andor Hajos, 6, Himfy u., 1114 Budapest; Marton Fekete, 49, Fo utca, 1027 Budapest; Marianna Kurti, 32, Nepstadion ut, 1143 Budapest; Tibor Lang, 11, Fenyo u, 1016 Budapest; Lajos Toldy, 53, Villanyi ut, 1118 Budapest; Janos Borvendeg, 19, Szeher ut, 1021 Budapest; Laszlo Nagy, 67, Pasareti ut, 1026 Budapest; Sandor Elek, 28, Dobo u, 1153 Budapest; Istvan Elekes, 28, Delej u, 1089 Budapest; Istvan Polgari, 1, Szabolcsu, 1134 Budapest, all of Hungary

[21] Appl. No.: 72,295

[22] Filed: Sep. 4, 1979

Related U.S. Application Data

[63] Continuation of Ser. No. 915,290, Jun. 9, 1978, abandoned, which is a continuation-in-part of Ser. No. 773,791, Mar. 2, 1977, abandoned.

[30] Foreign Application Priority Data

Mar. 2, 1976 [HU] Hungary .................. GO 1331

[51] Int. Cl.$^3$ ........................................... A61K 31/135
[52] U.S. Cl. ................................................. 424/330
[58] Field of Search ........................................ 424/330

[56] References Cited

U.S. PATENT DOCUMENTS 4,067,904  1/1978  Comer et al. ................. 424/330

FOREIGN PATENT DOCUMENTS 1337921  11/1973  United Kingdom .

OTHER PUBLICATIONS

Conn; Current Therapy (1977), pp. 216–217.

*Primary Examiner*—Allen J. Robinson
*Attorney, Agent, or Firm*—Young & Thompson

[57] ABSTRACT

1-tert.-butylamino-3-(2,5-dichlorophenoxy)-2-propanol and its pharmaceutically acceptable acid addition salts possess hypotensive and bradycardizing effects. Thus they can be applied in human therapy for the treatment of hypertension and simultaneously also of tachycardia.

1 Claim, No Drawings

TREATMENT OF HYPERTENSION WITH 1-TERT.-BUTYLAMINO-3-(2,5-DICHLOROPHENOXY)-2-PROPANOL

This is a continuation of application Ser. No. 915,290, filed June 9, 1978, now abandoned; which is a continuation-in-part application of Ser. No. 773,791, filed Mar. 2, 1977, now abandoned.

This invention relates to the use of 1-tert.-butylamino-3-(2,5-dichlorophenoxy)-2-propanol for the treatment of hypertension in humans.

It is generally known that a substantial part of cardiovascular diseases is connected with pathologic conditions involving hypertension. The development of hypertensive status causes an increase in cardiac output, which results e.g. in arrhythmia or tachycardia. It is therefore very desirable to find antihypertensive drugs which, in addition to their hypotensive effect, are also able to alleviate the heart work and its oxygen demand.

There are several known substances which exert a favorable influence on arrhythmia or tachycardia, but they have hardly detectable or even no hypotensive effects. Such substances are e.g. quinidine, procainamide (p-amino-N-/2-diethylaminoethyl/-benzamide hydrochloride), diphedan (5,5-diphenylhydantoine) and verapamil (α-isopropyl-α-[/N-methyl-N-homoveratryl/-γ-amino-propyl]-3,4-dimethoxy-phenylacetonitrile).

On the other hand, several antihypertensive agents or drugs are known and applied in therapy, which have no favorable influence on cardiac arrhythmia or tachycardia. Such substances are e.g. reserpine, guanethidine ([2-octahydro-1-azocinyl/-ethyl]-guanidine sulfate), methyldopa (α-methyl-3,4,-dihydroxyphenylalanine), clonidine (2-/2,6-dichlorophenylamine/-2-imidazoline hydrochloride) and hydralazine (1-hydrazino-phthalazine). It is particularly remarkable that e.g. hydralazine, one of the most widely used highly effective hypotensive agents, has just the undesired side-effect of provoking tachycardia. The same is true of minoxydil (6-amino-1-hydroxy-2-imino-4-piperidino-1,2-dihydropyrimidine), introduced more recently for therapy.

It has now been found that 1-tert.-butylamino-3-(2,5-dichlorophenoxy)-2-propanol and its pharmaceutically acceptable acid addition salts, when applied in the treatment of human pathologic conditions in which an abnormally high tension is connected with a tachycardial status, favorably decrease tension and also normalize cardiac rhythm (tachycardia). This compound is described in British Pat. No. 1,337,921.

The hypotensive effect of the compounds according to the invention is proved by several clinical tests. The tests were conducted by treating the patients initially with placebo, thereafter introducing the compound of the invention in increasing dosages, and finally, after adjusting the effective dosage, treating the patients again with placebo tablets. The results of these tests are summarized in Table 1.

TABLE 1

| Group | Mean daily dosage (mg) | Number of patients | Mean value of tension, mmHg At the end of the treatment period with placebo | Mean value of tension, mmHg At the end of the treatment period with the test compound | Decrease of tension, % |
|---|---|---|---|---|---|
| A | 21.78 | 16 | 167/100 | 132/83 | −20.9/−17.8 |
| B | 25.25 | 20 | 178/104 | 160/91 | −10.1/−12.5 |
| C | 16.25 | 24 | 180/100 | 152/86 | −15.6/−14.7 |

Remarks:
Group A: patients suffering from mild hypertension
Groups B and C: patients suffering from hypertension of medium degree The patients of Group C also received clopamide (N-/cis-2',6'-dimethyl-piperidyl/-3-sulfamyl-4-chlorobenzoic acid amide) in a daily dosage of 10 mg.

The data of Table 1 demonstrate that the compound of the invention, when applied alone, is effective in the treatment of mild or medium hypertension. When severe hypertension is to be treated, it is preferable to administer the compound along with another hypotensive agent. Depending on the severity of the disease, the effective oral dosage of the compound according to the invention is 0.1 to 1 mg/day/kg body weight, preferably 20 to 25 mg/day for adults. The required dosage can be decreased substantially by the conjoint administration of a diuretic agent.

The advantageous properties of the compound according to the invention, as compared to other substances of bradycardizing effect, are as follows:

Related to unit weight, this compound is one of the most potent bradycardizing agents, thus its therapeutic dosage level is low (5 to 30 mg/day when administered orally).

The compound exerts a prolonged effect; when administered in a single dose, its activity can be detected even 48 hours after administration. This prolonged effect cannot be attributed, however, to a slow resorption, since the bradycardizing effect first appears 20 to 90 minutes after oral administration, indicating a quick resorption of the compound in question.

The bradycardizing (i.e. negative chronotropic) effect of the compound is clearly isolated from the undesired negative inotropic effect, since the former is already substantial in such low dosages wherein the latter effect is insignificant. This is a particularly important advantage of the compound according to the invention, since the compound does not decrease myocardial strength when administered in therapeutical dosages.

The advantageous properties of the compound according to the invention, as compared to other hypotensive agents, are as follows:

In contrast to several other hypotensive agents applied in therapy, such as hydralazine (1-hydrazinophthalazine) and minoxydil (6-amino-1-hydroxy-2-imino-4-piperidino-1,2-dihydropyrimidine), the compound does not provoke tachycardia, thus it does not cause an increase in cardiac output; on the contrary, it slows down cardiac frequency and cardiac output and decreases the oxygen demand of the heart.

In contrast to several other hypotensive agents applied in therapy, such as guanethidine ([2-/octahydro-1-azocinyl/-ethyl]-guanidine sulfate) and its derivatives or prazosine (1-/4-amino-6,7-dimethoxy-2-quinazolinyl/-4-/2-furanylcarbonyl/-piperazine hydrochloride), the compound does not provoke orthostatic hypotension.

In contrast to several other hypotensive agents applied in therapy, such as reserpine, the compound is devoid of undesirable psychic (depression-provoking) side-effects.

In contrast to several other hypotensive agents applied in therapy, such as clonidine (2-/2,6-dichloroanilino/-2-imidazoline hydrochloride), the compound does not cause addiction.

In contrast to several other hypotensive agents applied in therapy, such as pindolol (4-/2-hydroxy-3-isopropylaminopropoxy/-indole), the compound has no sympathomimetic effect, i.e. it does not cause an increase in tension when administered in higher dosages.

The compound can be combined to advantage with other hypotensive agents, particularly with those having a peripheral point of attack, as well as with diuretics, and thus its relatively low effective dosage can be lowered further.

The following features are also remarkable:

The compound of the invention can also be applied to decrease hypertension not connected with tachycardia, i.e. the existence of tachycardia is not a pre-condition of the appearance of hypotensive effect.

The compound of the invention is also able to alleviate tachycardial states not connected with hypertension.

Consequently, the hypotensive and heart frequency reducing effects of the compound according to the invention are separate, independent activities which do not follow from one another. Besides the above, the following facts also prove the separate nature of hypotensive and bradycardizing effects:

The bradycardizing effect of the compound is first readily detectable 30 to 90 minutes after oral administration whereas in order to attain hypotensive effect a continuous administration of 7 to 10 days is required.

When the continuous oral administration of the compound is interrupted, its bradycardizing effect ceases within 24 to 48 hours, whereas its hypotensive effect persists for 7 to 10 days.

These facts also prove that the simultaneous existence of the bradycardizing and hypotensive effects of the compounds in question are unforeseeable.

1-tert.-butylamino-3-(2,5-dichlorophenoxy)-2-propanol contains an asymmetric carbon atom, thus it may exist in the form of optical isomers. The term "1-tert.-butylamino-3-(2,5-dichlorophenoxy)-2-propanol" embraces all of the possible enantiomers and enantiomeric mixtures of said compound.

1-tert.-butylamino-3-(2,5-dichlorophenoxy)-2-propanol and its pharmaceutically acceptable acid addition salts can be converted into pharmaceutical compositions by admixing the active agent with one or more conventional pharmaceutical excipient(s), such as carriers, diluents, surfactants, lubricating agents, disintegrating agents, salts for adjusting the osmotic pressure, preservatives, etc. These pharmaceutical compositions may be solids (e.g. tablets, capsules, pills, powders, etc.) or liquids (e.g. solutions, emulsions, suspensions, etc.), suitable for enteral or parenteral administration. The pharmaceutical compositions can be prepared by methods well known in the art.

The following Examples illustrate the receptures of some typical pharmaceutical compositions.

EXAMPLE 1

Pills for therapeutical purposes containing each 5 mg. of active substance, suitable for oral administration are prepared with the following composition:

| | |
|---|---|
| 1-tert.-butylamino-3-(2,5-dichlorophenoxy)-2-propanol hydrochloride | 0.00500 g. |
| Lactose | 0.05265 g. |
| Potato starch | 0.03455 g. |
| White gelatin | 0.00180 g. |
| Magnesium stearate | 0.00200 g. |
| Talc | 0.00300 g. |
| Aerosil-200 | 0.00100 g. |
| average weight: | 0.10000 g |

EXAMPLE 2

A solution for injection containing 1.5 mg. of active substance, suitable for parenteral therapeutic administration, is prepared with the following composition:

| | |
|---|---|
| 1-tert.-butylamino-3-(2,5-dichlorophenoxy)-2-propanol hydrochloride | 0.0015 g. |
| Sodium chloride | 0.0450 g. |
| Distilled water q.s. ad | 5 ml. |

What we claim is:

1. A method of treating hypertension arising from cardiovascular disease in humans, comprising administering to a human suffering from hypertension arising from cardiovascular disease 0.1 to 1 mg/kg body weight per day of a member selected from the group consisting of 1-tert.-butylamino-3-(2,5-dichlorophenoxy)-2-propanol and a pharmaceutically acceptable acid addition salt thereof.

* * * * *